(12) United States Patent
Wan et al.

(10) Patent No.: US 10,259,451 B2
(45) Date of Patent: Apr. 16, 2019

(54) MOTION SICKNESS MITIGATION SYSTEM AND METHOD

(71) Applicant: GM GLOBAL TECHNOLOGY OPERATIONS LLC, Detroit, MI (US)

(72) Inventors: Jingyan Wan, Sterling Heights, MI (US); Winson Ng, San Jose, CA (US); Mary E. Decaluwe, Oxford, MI (US); Mario Jodorkovsky, Nesher (IL)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 55 days.

(21) Appl. No.: 15/654,287

(22) Filed: Jul. 19, 2017

(65) Prior Publication Data

US 2019/0022347 A1    Jan. 24, 2019

(51) Int. Cl.
| | |
|---|---|
| *B60W 30/02* | (2012.01) |
| *A61M 21/00* | (2006.01) |
| *B60W 40/09* | (2012.01) |
| *B60W 40/08* | (2012.01) |
| *B60W 50/08* | (2012.01) |

(52) U.S. Cl.
CPC .......... *B60W 30/025* (2013.01); *A61M 21/00* (2013.01); *B60W 40/09* (2013.01); *B60W 50/08* (2013.01); *B60W 2040/0872* (2013.01)

(58) Field of Classification Search
CPC .... B60W 30/025; B60W 50/08; B60W 40/09; B60W 2040/0872; A61M 21/00
See application file for complete search history.

(56) References Cited

U.S. PATENT DOCUMENTS

| | | | | |
|---|---|---|---|---|
| 7,437,219 | B2* | 10/2008 | Bos | B60R 16/0232 701/1 |
| 2015/0120149 | A1* | 2/2015 | Worrel et al. | B60W 40/08 701/49 |
| 2017/0136842 | A1* | 5/2017 | Anderson et al. | B60G 17/016 |
| 2017/0267253 | A1* | 9/2017 | Schmidt et al. | B60W 2040/0872 |
| 2018/0052000 | A1* | 2/2018 | Larner et al. | B60W 30/025 |

* cited by examiner

*Primary Examiner* — Dale W Hilgendorf
(74) *Attorney, Agent, or Firm* — Lorenz & Kopf LLP

(57) ABSTRACT

Systems and methods are provided for mitigating motion sickness. When motion sickness is predicted, the motion sickness mitigation system alters vehicle performance, cabin conditions, and/or alerts the occupant to upcoming vehicle actions, to avoid or alleviate motion sickness. A controller includes a processor that receives an occupant profile and traffic information for an upcoming trip of the vehicle on a route. Using the occupant profile and the traffic information, the processor calculates whether the occupant will experience motion sickness when the vehicle travels on the route. A vehicle performance signal correlated to the calculation, is delivered by the processor to initiate motion sickness mitigation. The vehicle performance signal varies operation of a steering actuator, an acceleration actuator, and/or a brake actuator to implement the motion sickness mitigation.

20 Claims, 7 Drawing Sheets

MOTION SICKNESS MITIGATION SYSTEM AND METHOD

TECHNICAL FIELD

The present disclosure generally relates to systems and methods for mitigating motion sickness, and more particularly relates to motion sickness mitigation in a vehicle.

INTRODUCTION

Motion sickness may be described as a person's discomfort as a result of being subjected to movements, such as in a vehicle. Motion sickness may result in an ill feeling that may include nausea, headache, sweating or other symptoms. Motion sickness may result from a conflict between how different bodily senses respond to the movements, where one part of the body perceives motion differently than another part. Motion sickness may occur when a person is carried by a moving object such as a ground vehicle, plane, boat, or other by other means of transport. Motion sickness is a relatively common affliction and may result in negative experiences for individuals otherwise engaged in positive activities.

Accordingly, it is desirable to provide systems and methods that mitigate motion sickness. Furthermore, other desirable features and characteristics of the present invention will become apparent from the subsequent detailed description and the appended claims, taken in conjunction with the accompanying drawings and the foregoing technical field and introduction.

SUMMARY

Systems and methods are provided for motion sickness mitigation. In various embodiments, a motion sickness mitigation system of a vehicle includes a steering system with a steering actuator for steering the vehicle through the steering system. An accelerator system including an accelerator actuator actuating the braking system may be included. A braking system including a brake actuator actuating the braking system may be included. A controller includes a processor configured to receive an occupant profile and traffic information for an upcoming trip of the vehicle on a route. The occupant profile includes a biometric condition of an occupant, preferences of the occupant and historical travel information of the occupant in the vehicle. Using the occupant profile and the traffic information, the processor calculates whether the occupant will experience motion sickness when the vehicle travels on the route. A vehicle performance signal correlated to the calculation, is delivered by the processor to initiate motion sickness mitigation. The vehicle performance signal varies operation of the steering actuator, the acceleration actuator, and/or the brake actuator to implement the motion sickness mitigation.

In another embodiment, the motion sickness mitigation system includes a suspension system and a suspension actuator through which the suspension system is varied. The vehicle performance signal varies operation of the suspension actuator to implement the motion sickness mitigation.

In another embodiment, the motion sickness mitigation system includes a transceiver through which information is received by the controller. The processor is configured to enter the information into the occupant profile.

In another embodiment, the processor is configured to carry out the calculation prior to the vehicle starting on the route.

In another embodiment, occupant state devices provide an occupant state input signal to the processor representing at least one state of the occupant. The processor calculates an occupant motion sickness value based on the occupant state input signal. The occupant motion sickness value is indicative of a likelihood that the occupant will experience motion sickness.

In another embodiment, an accelerometer monitors acceleration of the vehicle and provides a first vehicle state signal to the processor based on the acceleration, when the vehicle operates on the route. A steering angle sensor monitors steering changes of the vehicle and provides a second vehicle state signal to the processor based on the steering changes, when the vehicle operates on the route. A suspension sensor on the vehicle monitors suspension oscillations and provides a third vehicle state signal to the processor based on the suspension oscillations, when the vehicle operates on the route. The processor calculates a vehicle motion sickness value based on the first, second and third vehicle state signals. The vehicle motion sickness value is indicative of a likelihood that the occupant will experience motion sickness.

In another embodiment, the processor comprises a pre-trip prediction module and a driving induced motion sickness prediction module. The pre-trip prediction module receives the occupant profile and the traffic information and calculates whether the occupant will experience motion sickness when the vehicle travels on the route. The driving induced motion sickness prediction module receives the first, second and third vehicle state signals and calculates the vehicle motion sickness value.

In other embodiments, a method of motion sickness mitigation in a vehicle includes the processor receiving a data input signal that represents an occupant profile. The occupant profile includes a biometric condition of an occupant, preferences of the occupant, and historical travel information of the occupant in the vehicle. The processor receives an off-board input signal representing traffic status for an upcoming trip of the vehicle on a route. The processor calculates whether the occupant will experience motion sickness when the vehicle travels on the route, using the data input signal and the off-board input signal. The processor delivers a vehicle performance signal correlated to the calculation to initiate motion sickness mitigation. The vehicle performance signal varies operation of a steering actuator of the vehicle, an accelerator actuator of the vehicle, and/or a brake actuator of the vehicle when the vehicle operates on the route, to implement the motion sickness mitigation.

In another embodiment, a suspension system of the vehicle includes a suspension actuator through which the suspension system is varied. Operation of the suspension actuator is altered via the vehicle performance signal, to implement the motion sickness mitigation.

In another embodiment, the processor receives information from the occupant via a transceiver. The processor delivers the information to a storage device for storage in the occupant profile.

In another embodiment, prior to the vehicle starting on the route, the processor calculates whether the occupant will experience motion sickness when the vehicle travels on the route.

In another embodiment, an occupant state input signal is delivered to the processor by occupant state devices. The occupant state input signal represents at least one state of the occupant. An occupant motion sickness value ($MSV_o$) is calculated based on the occupant state input signal. The occupant motion sickness value is indicative of a likelihood that the occupant will experience motion sickness.

In another embodiment, the $MSV_o$ is calculated using and occupant's heart rate, respiration rate, skin resistance, skin temperature, blood pressure and facial expression.

In another embodiment, an accelerometer monitors acceleration of the vehicle when the vehicle operates on the route. A first vehicle state signal based on the acceleration is delivered to the processor. A steering angle sensor monitors steering changes of the vehicle when the vehicle operates on the route. A second vehicle state signal based on the steering changes is delivered to the processor. A suspension sensor monitors suspension oscillations of the vehicle when the vehicle operates on the route. A third vehicle state signal based on the suspension oscillations is delivered to the processor. The processor calculates a vehicle motion sickness value ($MSV_v$) based on the first, second and third vehicle state signals.

In another embodiment, sensing devices monitor cabin conditions of the vehicle. The processor calculates a cabin condition state value (C) based on the cabin conditions. The C is indicative of a likelihood that the occupant will experience motion sickness.

In another embodiment, the processor calculates an aggregate motion sickness value (MSV) by the equation $MSV=MSV_v \times MSV_o \times C$. The MSV is indicative of a likelihood that the occupant will experience motion sickness.

In another embodiment, the motion sickness mitigation is implemented when the MSV exceeds a threshold value.

In another embodiment, the motion sickness mitigation includes activating a display to alert the occupant to an upcoming vehicle maneuver to avoid a mismatch between sensed movements of the vehicle by the occupant.

In another embodiment, the display includes a visual display system, an audible display system and a haptic display system. An occupant state input signal is delivered by occupant state devices to the processor. The occupant state input signal represents states of the occupant. The processor evaluates the states of the occupant to discern a gaze, a position, and an occupation of the occupant. The processor selects among the visual display system, the audible display system and the haptic display system based on the gaze, the position and the occupation.

In additional embodiments, a motion sickness mitigation system of vehicle includes an acceleration sensor sensing acceleration of the vehicle and generating an acceleration signal representative of the sensed acceleration. A camera observes an occupant and provides a visual signal representative of the occupant. A controller receives the acceleration signal and the visual signal and includes a processor. An actuator device is responsive to the processor and controls performance of a vehicle system. The processor calculates whether the occupant will experience motion sickness based on the acceleration signal and the visual signal. The processor controls the actuator device in a variable manner depending on whether the calculation indicates the occupant will experience motion sickness.

BRIEF DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the application or its uses. Furthermore, there is no intention to be bound by any expressed or implied theory presented in the preceding technical field, introduction, brief summary or the following detailed description. As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein are merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Figure 1:
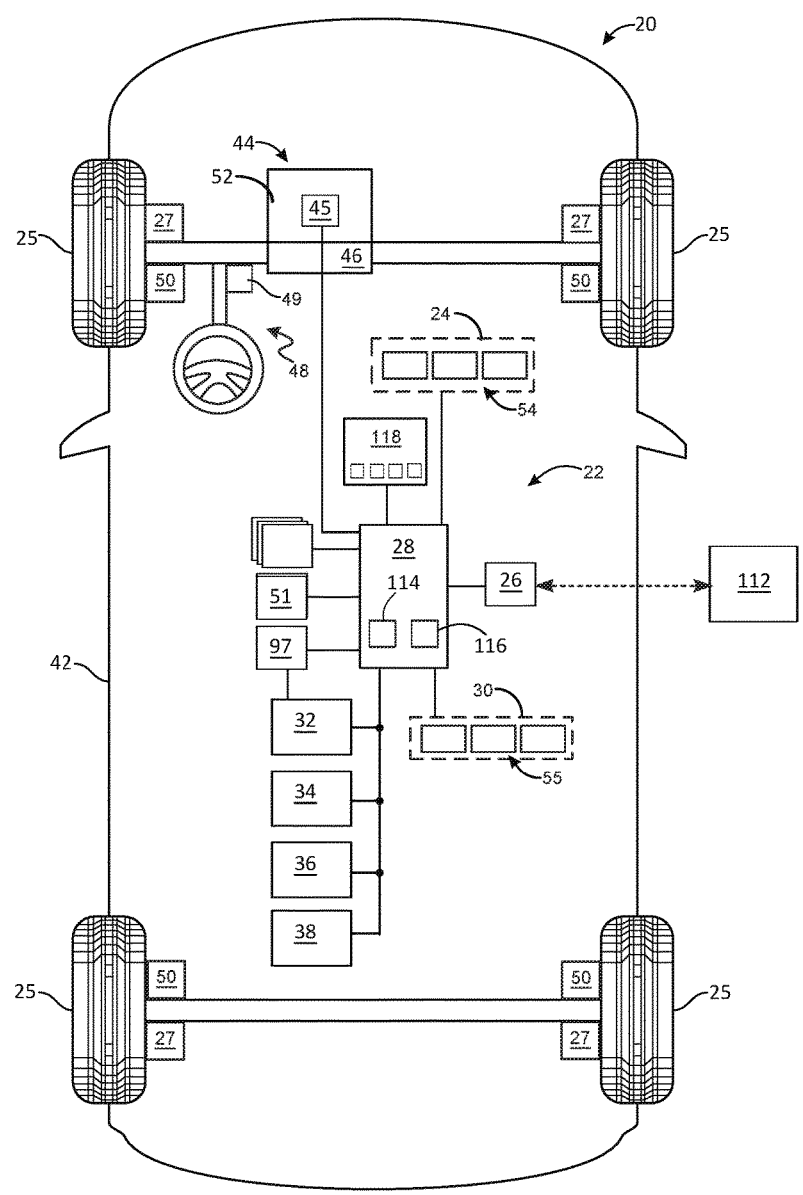
FIG. 1 is a functional block diagram illustrating a control system of a vehicle employing methods, in accordance with various embodiments.

FIG. 1 illustrates a device for transporting occupants, according to an exemplary embodiment. In the current example, the device is a vehicle 20 and specifically, is a ground vehicle such as an automobile of any one of a number of different types. In other embodiments, the vehicle 20 may be a plane, boat or other type of mobile device. As described in greater detail below, the vehicle 20 includes a motion sickness mitigation system 22 for predicting and/or mitigating motion sickness of occupants of the vehicle 20. Generally, as discussed further below, the motion sickness mitigation system 22 receives inputs from sources off-board and on-board the vehicle 20, processes the inputs, and provides outputs to mitigate motion sickness, which may include controlling operation of the vehicle 20. In the depicted embodiment, the motion sickness mitigation system 22 generally includes, or cooperates with a sensing system 24, a communication system 26, a controller 28, an actuator system 30, a vehicle state system 32, an occupant state system 34, an interface system 36, and additional vehicle systems 38. These various parts of the motion sickness mitigation system 22 are described in greater detail below along with other features and aspects. In various embodiments, the motion sickness mitigation system 22 performs various steps as set forth further below in connection with the processes 200, 300 and 400 of FIGS. 3, 5 and 6, respectively.

As depicted in FIG. 1, the vehicle 20 generally includes a body 42, supported on wheels 25 by a suspension system 27. The body 42 substantially encloses components of the vehicle 20, and the wheels 25 are each rotationally coupled near a respective corner of the body 42. In various embodiments, the vehicle 20 is an autonomous vehicle and the motion sickness mitigation system 22 is incorporated into the autonomous vehicle and influences the autonomous control to mitigate motion sickness. The vehicle 20 is, for example, a vehicle that is automatically controlled to carry occupants from one location to another. In some embodiments, the vehicle 20 has a so-called Level Four or Level Five automation level. A Level Four system indicates "high automation", referring to the driving mode-specific performance by an automated driving system of all aspects of the dynamic driving task, even if a human driver does not respond appropriately to a request to intervene. A Level Five system indicates "full automation", referring to the full-time performance by an automated driving system of all aspects of the dynamic driving task under all roadway and environmental conditions that can be managed by a human driver.

As shown, the vehicle 20 has various vehicle systems that generally include a propulsion system 44 with an accelerator system 45 and a transmission system 46, a steering system 48, and a brake system 50. The propulsion system 44 may, in various embodiments, include a power unit 52 such as an internal combustion engine, an electric machine such as a motor, a fuel cell and/or another power source. The transmission system 46 may be configured to transmit power from the power unit 52 to one or more of the vehicle wheels 25 according to selectable speed ratios. According to various embodiments, the transmission system 46 may include a step-ratio automatic transmission, a continuously-variable transmission, or other appropriate transmission. The accelerator system 45 is configured to activate the propulsion system 44 to accelerate the vehicle 20 and to decelerate the vehicle 20. The accelerator system 45 may respond to driver inputs, or may respond to the controller 28. The accelerator system 45 may include a throttle, such as with an internal combustion engine, electric control, such as with an electric vehicle, or another mechanism to control acceleration. The brake system 50 is configured to provide braking torque to the vehicle wheels 25. The brake system 50 may, in various embodiments, include friction brakes, brake by wire, a regenerative braking system such as an electric machine, and/or other appropriate braking systems. The steering system 48 influences a position of the vehicle wheels 25. The accelerator system 45, the brake system 50 and steering system 48 receive inputs from the driver via an accelerator pedal (not depicted), a brake pedal (not depicted), and steering wheel or from the actuator system 30 in autonomous operation. While depicted as including a steering wheel for illustrative purposes, in some embodiments contemplated within the scope of the present disclosure, the steering system 48 is automated and may not include a steering wheel.

Figure 2:
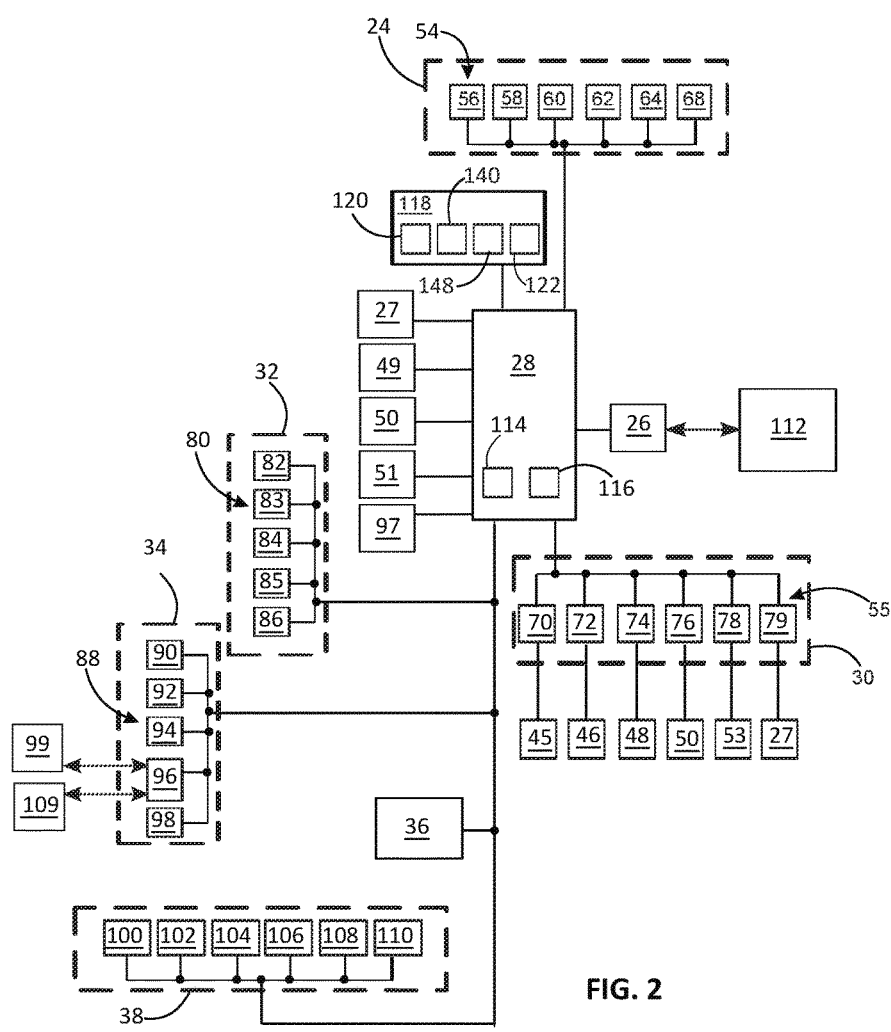
FIG. 2 is a block diagram illustrating a motion sickness mitigation system of the vehicle of FIG. 1 employing methods, in accordance with various embodiments.

With additional reference to FIG. 2, the sensing system 24 includes one or more sensing devices 54 that sense observable conditions of the exterior environment of the autonomous vehicle 10. The sensing devices 54 may include, but are not limited to, radar 56, lidar 58, a global positioning system 60, cameras 62, ultrasonic sensors 64, and/or other sensors 68. The sensing devices 54 may each be communicatively coupled with the controller 28 and may each provide a signals and/or other information thereto. The actuator system 30 includes one or more actuator devices 55 that control one or more vehicle operations or features such as, but not limited to, an accelerator actuator 70 of the accelerator system 45 for the propulsion system 44, a shift actuator 72 of the transmission system 46, a steering actuator 74 of the steering system 48, a brake actuator 76 of the brake system 50, a suspension actuator 79 of the suspension system 27, or other actuators 78 for other vehicle systems 53. The actuator devices 55 may each be communicatively coupled with the controller 28 to receive signals therefrom, directly, or indirectly such as through intermediary modules or controllers, and to provide information thereto, when relevant, such as feedback. The vehicle state system 32 includes one or more sensors 80 that sense or measure conditions of the vehicle 20, or of a vehicle system. The sensors 80 may include, but are not limited to, acceleration/deceleration sensors 82 for sensing longitudinal and/or later acceleration of the vehicle 20, an odor sensor 83, speed sensors 84, such as a revolution per minute sensor for the transmission 46, a light sensor 85, and a suspension sensor 86 such as a displacement or position sensor for sensing the oscillation of the suspension system 27. The occupant state system 34 includes one or more occupant state devices 88 that provide information or data on aspects of an occupant of the vehicle 20. The occupant state devices 88 may include, but are not limited to, biometric sensors 90 for sensing biological features of an occupant, motion sensors 92 for sensing motion of an occupant, cameras 94 for observing features of an occupant, a transceiver 96 for connecting with an occupant's personal electronic device(s) PED 99 to obtain data on the occupant, and an interface 98 to receive inputs from an occupant such as temperature, aroma and lighting preferences. The inputs may be received as alphanumeric entries, or a voice response system may be used. In a number of examples, the interface 98 may comprise one or more sensors associated with user interfaces such as vehicle touch screens, rotary knobs, buttons, and/or other types of user interfaces within the vehicle 20 for receiving inputs from an occupant. A vision system 97 may be configured to recognize aspects of an occupant using inputs from the occupant state devices 88. The controller 28, may support any number of additional operations and functions of additional vehicle systems 38 in the vehicle 20 used in, or associated with, the motion sickness mitigation system 22. In various embodiments, the additional vehicle systems 38 include a heating, ventilation and air conditioning (HVAC) system 100, a lighting system 102, an audio display system 104, a visual display system 106, a haptic display system 108, a navigation system 110. In other embodiments, the vehicle features can further include interior and/or exterior vehicle features such as, but are not limited to, doors, a trunk, and cabin features, etc. (not numbered). The controller 28 may receive information from any number of additional sensors, which may include for example, a steering angle sensor 49, roll, pitch, and yaw sensor(s) 51, wheel speed sensors, various sensors for the propulsion system 44, a vehicle speed sensor, various temperature sensors, position sensors, etc.

The communication system 26 is configured to wirelessly communicate information to and from other entities 112, such as but not limited to, other vehicles ("V2V" communication,) infrastructure ("V2I" communication), remote systems, and/or personal devices. In an exemplary embodiment, the communication system 26 is a wireless communication system configured to communicate via a wireless local area network (WLAN) using IEEE 802.11 standards or by using cellular data communication. However, additional or alternate communication methods, such as a dedicated short-range communications (DSRC) channel, are also considered within the scope of the present disclosure. DSRC channels refer to one-way or two-way short-range to medium-range wireless communication channels specifically designed for automotive use and a corresponding set of protocols and standards.

The controller 28 may accept information from various sources, process that information, and provide control commands based thereon to effect outcomes such as operation of the vehicle 20 and its systems, including the motion sickness mitigation system 22. In the depicted embodiment, the controller 28 includes a processor 114, a memory device 116, and is coupled with a storage device 118. The processor 114 performs the computation and control functions of the controller 28, and may comprise any type of processor or multiple processors, single integrated circuits such as a microprocessor, or any suitable number of integrated circuit devices and/or circuit boards working in cooperation to accomplish the functions of a processing unit. During operation, the processor 114 executes one or more programs 120 that may be contained within the storage device 118 and, as such, controls the general operation of the controller 28, generally in executing the processes described herein, such as the processes 200, 300 and 400 described further below in connection with FIGS. 3, 5 and 6.

The memory device 116 may be any type of suitable memory. For example, the memory device 116 may include volatile and nonvolatile storage in read-only memory (ROM), random-access memory (RAM), and keep-alive memory (KAM), for example. KAM is a persistent or non-volatile memory that may be used to store various operating variables while the processor 114 is powered down. The memory device 116 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 28. In certain examples, the memory device 116 is located on and/or co-located on the same computer chip as the processor 114. In the depicted embodiment, the storage device 118 stores the above-referenced programs 120 along with one or more stored values 122.

The storage device 118 stores data for use in automatically controlling the vehicle 20 and its systems. The storage device 118 may be any suitable type of storage apparatus, including direct access storage devices such as hard disk drives, flash systems, floppy disk drives and optical disk drives. In one exemplary embodiment, the storage device 118 comprises a source from which the memory device 116 receives the programs that execute one or more embodiments of one or more processes of the present disclosure, such as the steps of the processes 200, 300, 400 (and any sub-processes thereof) described further below in connection with FIGS. 3, 5 and 6. In another exemplary embodiment, the program may be directly stored in and/or otherwise accessed by the memory device 116. The programs represent executable instructions, used by the electronic controller 28 in processing information and in controlling the vehicle 20 and its systems. The instructions may include one or more separate programs, each of which comprises an ordered listing of executable instructions for implementing logical functions. The instructions, when executed by the processor 114 support the receipt and processing of signals such as from sensors, perform logic, calculations, methods and/or algorithms for automatically controlling the components and systems of the vehicle 20. The processor 114 may generate control signals for the actuator system 30 to automatically control the components of the vehicle 20 in autonomous mode based on the logic, calculations, methods, and/or algorithms.

While the components of the motion sickness mitigation system 22 are depicted as being part of the same system, it will be appreciated that in certain embodiments these features may comprise multiple systems. In addition, in various embodiments the motion sickness mitigation system 22 may comprise all or part of, and/or may be coupled to, various other vehicle devices and systems, such as, among others, the sensing system 24, the actuator system 30, and/or one or more other systems of the vehicle 20.

Figure 3:
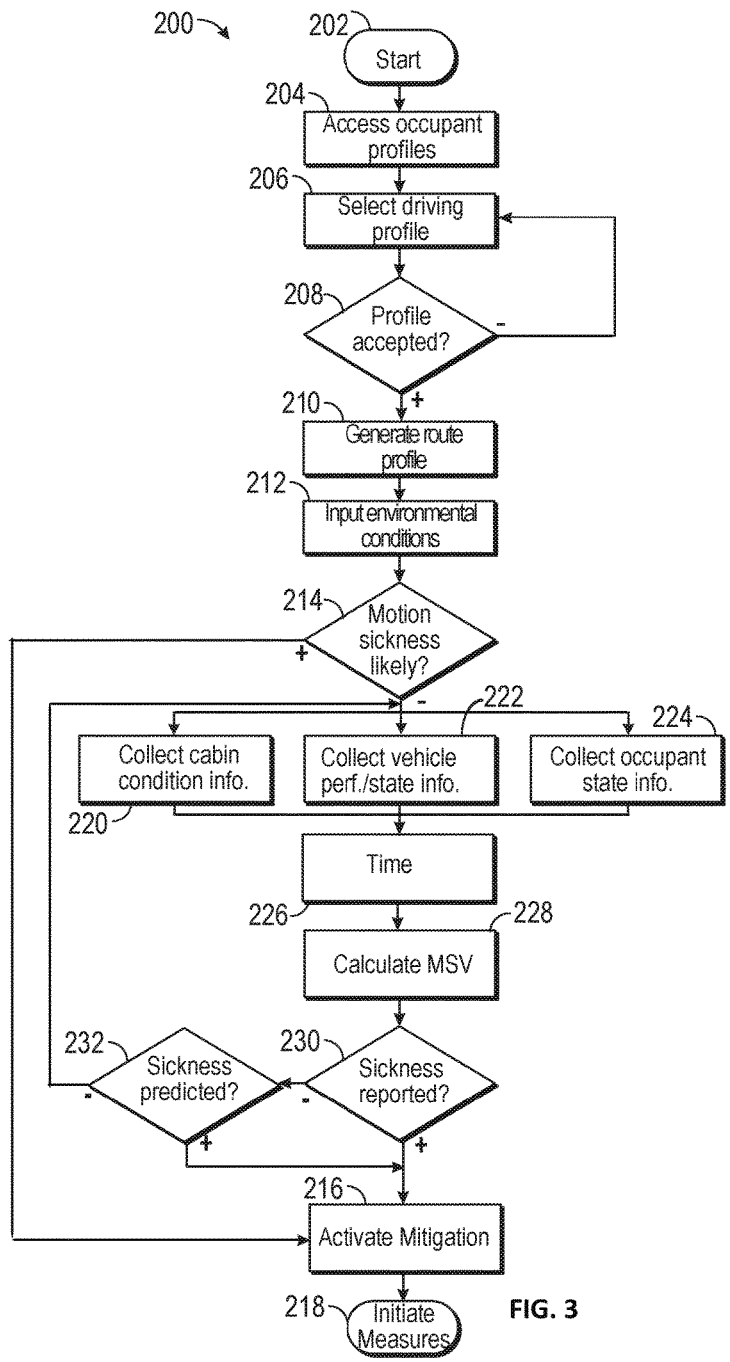
FIG. 3 is a flowchart illustrating a process employing motion sickness mitigation methods for controlling the vehicle of FIG. 1, in accordance with various embodiments.

For an exemplary embodiment, FIG. 3 illustrates a flowchart of a process 200 for mitigating motion sickness of an occupant of the vehicle 20. The process 200 is implemented in connection with the vehicle 20, including the motion sickness mitigation system 22 and other systems, sub-systems, and components thereof, including those illustrated in FIGS. 1 and 2, in accordance with the exemplary embodiment. The process 200 is also discussed below in connection with FIG. 4, which depicts an illustrative control system 130, such as may be implemented by the controller 28.

Figure 4:
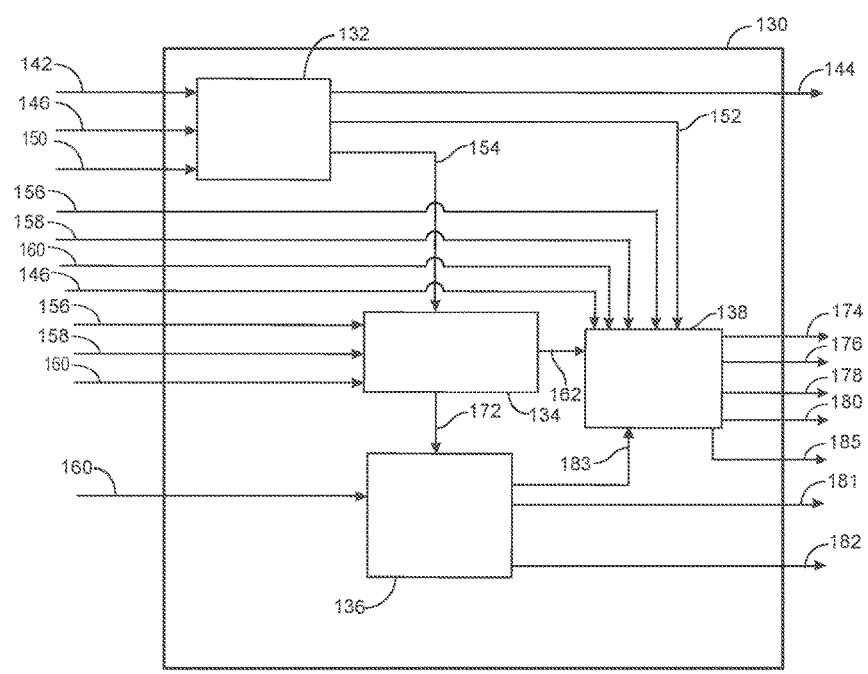
FIG. 4 is a dataflow diagram illustrating a part of the motion sickness mitigation system of the vehicle of FIG. 1, in accordance with various embodiments.

In various embodiments, one or more instructions may be embodied in the controller 28 and, when executed by the processor 114, effect operation of the motion sickness mitigation system 22. As illustrated in FIG. 4, a functional block diagram with dataflows illustrates various embodiments of a control system 130 that may be embedded within the controller 28 for operation of the motion sickness mitigation system 22. Various embodiments may include any number of sub-modules embedded within the controller 28, and/or other controllers. As can be appreciated, the sub-modules shown in FIG. 4 may be combined and/or further partitioned to similarly effect motion sickness mitigation for an occupant. Inputs to the control system 130 may be delivered from other parts of the motion sickness mitigation system 22, from off-board sources such as entities 112 shown in FIG. 1, from other systems of the vehicle 20, such as may be received from other control modules (not shown), from the memory device 116/storage device 118, and/or may be determined/modeled by other sub-modules (not shown) within the controller 28. In various embodiments, the control system 130 includes a pre-trip prediction module 132, a driving induced motion sickness prediction module 134, an interface modality module 136, and a mitigation module 138. Further details of the control system 130 are described below along with the process 200.

With reference to FIGS. 3 and 4, the process 200 is initiated at step 202. For example, in various embodiments, the process 200 may be initiated when the vehicle 20 enters a start mode, or when an occupant enters the vehicle 20. In one embodiment, the process 200 is initiated when a driver has engaged an ignition of the vehicle 20. Proceeding to step 204, the process 200 accesses occupant profiles 148 that may exist for current occupants of the vehicle 20 via a data signal provided to the pre-trip prediction module 132. An occupant profile 148 may be stored in the storage device 118 and is built using information such as historical travel information, health conditions, motion sickness susceptibility to motion sickness, and mitigation preferences for a particular occupant. Information for the occupant profile 148 is obtained, for example, via the transceiver 96 through connection with tan occupant's PED 99 to obtain data on the occupant, and/or through the interface 98 to receive inputs from the occupant. The transceiver 96 may obtain information, such as from applications on the PED 99 including health applications, that share information on the occupant such as risk factors (age, sleep patterns, food and drink consumption, etc.), and may obtain social media activity, internet postings, etc. to assist in building the occupant profile 148 using an occupant's activities. The occupant profile 148 may also include survey/question responses provided by the occupant and obtained from the storage device 118 or in real time through the interface 98. The occupant may also similarly provide information such as temperature, aroma and lighting preferences for mitigation measures, and other selections through the driving profile signal 150 delivered to the pre-trip prediction module 132.

Proceeding to step 206, a driving profile 140 is selected by the pre-trip prediction module 132 such as from the storage device 118. The driving profile 140 is an option selected from a list of preprogrammed commands for how the vehicle 20 will perform when operating in autonomous control and is received by the pre-trip prediction module 132 through the driving profile signal 150. For example, magnitude limits of normal operation of steering speed and longitudinal/lateral acceleration and deceleration may vary by option. In addition, suspension setting stiffness may vary by option. Preferred seat position/orientation for the occupant may be included in the driving profile signal 150. Route planning rules may also be included such as to avoid bumpy roadways, or roads with a greater number of curves, speed changes, traffic etc. The pre-trip prediction module 132 selects the driving profile 140 based on the occupant profile 148, and weighs factors such as the occupant's susceptibility to motion sickness. For example, if the occupant profile 148 indicates a low susceptibility to motion sickness, an aggressive driving profile may be selected. At step 208, a determination is made as to whether the occupant accepts the selected driving profile 140. For example, the selected driving profile 140 is displayed through the interface 98 via a verify signal 144 from the pre-trip prediction module 132. The occupant may enter agreement, or select a different option. When the occupant rejects the selected driving profile 140, the process 200 may return to step 206 where another driving profile is selected. When the occupant accedes to the selected driving profile 140 at step 208, the process 200 proceeds, and through step 210, a route profile is generated by the pre-trip prediction module 132 using the off-board input signal 142, the data input signal 146, and the driving profile signal 150. The off-board input signal 142 includes information obtained through the communication system 26, such as traffic information. The data input signal 146 may include information such as time of day to assist in determining projected traffic patterns. The driving profile signal includes information such as route planning rules. The input signals 146/142 may also include trip start and end locations, and route details, such as from a map application, such as in the navigation system 110, and traffic status information, such as is obtained from the other entities 112. At step 212, environmental conditions are provided to the pre-trip prediction module 132, such as through the off-board input signal 142, or from the additional vehicle systems 38 that include a temperature sensor or a weather application.

A determination is made as to whether the occupant is predicted to experience motion sickness at an early stage of the trip at step 214. Using the information obtained through steps 204-212, the pre-trip prediction module 132 makes the determination. More specifically, factors indicating the occupant is at increased risk to experience motion sickness at early stage of the trip include the occupant's motion sickness susceptibility, such as based on age and other factors obtained from the occupant profile 148. The factors indicating the occupant is at increased risk to experience motion sickness at early stage of the trip may include: whether the occupant has experienced motion sickness at an early stage of a previous trip of which the occupant profile, driving profile, route profile, and environmental situation are similar to those currently expected; whether the occupant experienced motion sickness at early stage of a previous trip of which the occupant profile, driving profile, route profile, and/or environmental situation are different than those currently expected, and the occupant's health condition (as collected through the data input signal 146), in the current trip is worse than in the previous trip; the occupant's preferred mitigation didn't work in the previous trip; the occupant chooses a more aggressive driving profile for the upcoming current trip; the route of the upcoming current trip includes more vehicle behavior changes, e.g. stop-and-go, turns, lane changes; the duration of the upcoming current trip is longer (e.g. from GPS); and/or the route profile/environmental situation from steps 210, 212 is worse in the upcoming current trip, e.g. bumpy road, raining, rush hour (from GPS or off-board input signal 142). In other examples, the factors indicating the occupant is at increased risk to experience motion sickness at early stage of the trip include instances where the occupant has not experienced motion sickness at early stage of a previous trip of which the occupant profile, driving profile, route profile, and/or environmental situation are different, and two or more of the following conditions are expected to happen in the current trip: the occupant's health condition in the upcoming current trip is worse than in the previous trip; the occupant's preferred mitigation didn't work in the previous trip; the occupant chooses a more aggressive driving profile for the upcoming current trip; the route of the upcoming current trip includes more vehicle behavior changes, e.g. stop-and-go, turns, lane changes, etc.; the duration of the upcoming current trip is longer; and/or the route profile/environmental situation from steps 210, 212 is projected to be worse for the upcoming current trip, e.g. bumpy road, raining, rush hour. In a number of embodiments, for the determination at step 214, the occupant is less likely to experience motion sickness at early stage of the trip if: the occupant has not experienced motion sickness at early stage of the previous trip of which the occupant profile, driving profile, route profile, and/or environmental situation are similar to the upcoming current trip. In addition, weights may be assigned to the factors in the occupant profile, driving profile, route profile, and environmental situation based on their expected contribution to motion sickness. For example, a lack of sleep may be given greater weight than weather, and previous motion sickness history may be given greater weight than traffic. The weights of each factor may be adjusted after each trip according to the occupant's response (whether they experience sickness at the early stage), as indicated by the occupant through the interface 98. Therefore, the prediction of motion sickness at the early stage of the trip may provide increased accuracy when the number of trips in the vehicle 20 increases for each occupant. At step 214, the pre-trip prediction module 132 scores the likelihood of motion sickness being experienced at an early stage of the trip based on the presence of the foregoing factors and their respective weights. When the determination is positive at step 214, the process 200 proceeds to step 216 and motion sickness mitigation is activated. The pre-trip prediction module 132 sends a mitigate signal 152 to the mitigation module 138 to initiate mitigation measures at step 218 as further described below. It should be appreciated that in the current embodiment, steps 202-214 occur prior to moving operation of the vehicle 20, and are based on information and data available at that the pre-trip stage. Step 216 may also be carried out at the pre-trip stage when activated by the pre-trip prediction module 132. Accordingly, the motion sickness mitigation system 22 initiates mitigation measures before the vehicle 20 begins to move, at a stage where occupant motion sickness has not yet been influenced by movement of the vehicle 20. In other embodiments, some of the steps 202-216 may be conducted shortly after the vehicle 20 begins to move, but at an early stage of a trip.

When the determination is negative at step 214, meaning early stage motion sickness is not predicted, the pre-trip prediction module 132 provides an initiate signal 154 to the driving induced motion sickness prediction module 134 to initiate operation. As determined at step 214, motion sickness was not predicted at an early stage of the trip and therefore mitigation was not initiated at the start of the trip, however, the motion sickness mitigation system 22 through the process 200 continues to monitor for indications of occupant motion sickness. The process 200 proceeds to steps 220, 222 and 224 to collect information for real time motion sickness prediction after initiation of the current trip by the vehicle 20. Steps 220, 222, 224 may be conducted serially or in parallel. At step 220, cabin conditions of the vehicle 20 are provided to the driving induced motion sickness prediction module 134 through the cabin conditions signal 156 supplied by the additional vehicle systems 38 and/or the sensors 80. For example, cabin temperature, and airflow rates may be supplied by the HVAC system 100, window positions, and air quality/aromas and light conditions may be supplied by various sensors, such as the sensors 83, 85. The cabin conditions signal 156 supplies information on the foregoing and other factors that may contribute to an occupant's susceptibility to motion sickness. At step 222, the process 200 monitors vehicle performance and a vehicle state input signal 158 is supplied to the driving induced motion sickness prediction module 134. The vehicle state input signal 158 may be a combination of a number of signals for different vehicle functions. For example, longitudinal and lateral acceleration values are supplied from the acceleration/deceleration sensors 82, steering angle variations are supplied from the steering angle sensor 49, and suspension settings and/or suspension displacement are supplied by the suspension system 27. In addition, route planning information is supplied, such as from the pre-trip prediction module 132 through the signal 154. The vehicle state input signal 158 and the route plan supplies information on factors that may contribute to an occupant's susceptibility to motion sickness. At step 224, occupant state information is supplied to the driving induced motion sickness prediction module 134, such as through the occupant state input signal 160. For example, biometric information of the occupant may be supplied by the biometric sensors 90, information on facial expression, point of gaze, head movement, and non-driving task engagement may be supplied by the interior motion sensors 92, the interior cameras 94, and/or from the occupant's PED 99 through the transceiver 96. The occupant state input signal 160 is indicative of the occupant's susceptibility to motion sickness in the current trip of the vehicle 20. In a number of embodiments, information from the sensing system 54, which shows surrounding traffic activity, is used to predict upcoming maneuvers of the vehicle 20 such as steering or braking. Increased activity increases an occupant's risk of incurring motion sickness.

At step 226, the process 200 includes a timer to allow time to accumulate before proceeding so that sufficient data and information is collected at steps 220, 222 and 224. At step 228, the process 200 predicts the likelihood that the occupant will experience motion sickness in the current trip, based on the results of steps 220, 222 and 224. Example factors include facial expression, where a disgusted appearance indicates susceptibility to motion sickness. Head tracking indicating rapid movement also indicates increased susceptibility. An eye gaze looking at the road ahead indicates a lower susceptibility. An occupant posture of relining also indicates a lower susceptibility.

In a number of examples, a motion sickness value associated with the vehicle states ($MSV_v$) is calculated from the vehicle state input signal 158, such as by using the integral of the squared frequency weighted accelerations of x, y, and z axis, and roll, pitch, and yaw, using the vehicle state input signal 158 supplied by the acceleration/deceleration sensors 82 and the roll, pitch and yaw sensor(s) 51. This is represented by the equation:

$$MSV_v = \sqrt{\int a_f^2 \cdot dt}$$

where $a_f$ is the combined acceleration in the x, y and z axis and roll, pitch and yaw.

Also at step 228, in a number of examples, road tests are conducted and the results associate occupant state with motion sickness level, where S indicates susceptibility, HR indicates heart rate, RSP indicates respiration rate, GSR indicates skin resistance, TEMP indicates skin temperature, BP indicates blood pressure, Facial indicates facial expression ("disgust" will be used among various expressions), Mismatch indicates sensory mismatch between visual and body perceived movement and this mismatch will be influenced by body/head/eye movement. An occupant motion sickness value based on occupant state ($MSV_o$) is calculated for the current trip from the occupant state input signal 160 of step 224 using the expression:

$$MSV_o = f(S, HR, RSP, GSR, TEMP, BP, Facial, Mismach) \cdot t$$

where t is the time of the trip from start to end.

Also at step 228, in a number of examples, the cabin conditions from step 220 are used to determine a cabin condition state value (C), which is a function of temperature (T), airflow (F), odors (O) and ambient light (L) using the expression:

$$C = \Psi(T,F,O,L)$$

Accordingly, at step 228 an aggregate motion sickness value (MSV) is calculated by the driving induced motion sickness prediction module 134 using the equation:

$$MSV = MSV_v \times MSV_o \times C$$

The process 200 proceeds to step 230 where a determination is made as to whether the occupant is reporting motion sickness such as by entering a positive value through the interface 98. When the determination at step 230 is positive and the occupant is reporting motion sickness, the process proceeds to step 216 and motion sickness mitigation is activated, such as by a mitigate signal 162 from the driving induced motion sickness prediction module 134 to the mitigation module 138, regardless of the MSV value, and at step 218 mitigation is conducted. When the determination at step 230 is negative and the occupant has not reported motion sickness, the process 200 proceeds to step 232. The driving induced motion sickness prediction module 134 evaluates the MSV calculated at step 228 to predict the likelihood of motion sickness of the occupant. For example, the calculated MSV may be compared to MSV values stored in the storage device 118 that are indicative of motion sickness occurring. In some examples this may be done using lookup tables of stored MSV values, or by comparing the calculated value to a threshold. When the comparison indicates the calculated MSV is not indicative of motion sickness, the process 200 returns to steps 220, 222, 224 and ongoing monitoring and evaluation is conducted. When the comparison at step 232 indicates that motion sickness is likely to occur, the process proceeds to step 216 where motion sickness mitigation is activated, such as by the mitigate signal 162 from the driving induced motion sickness prediction module 134 to the mitigation module 138, and at step 218 mitigation is conducted.

Figure 5:
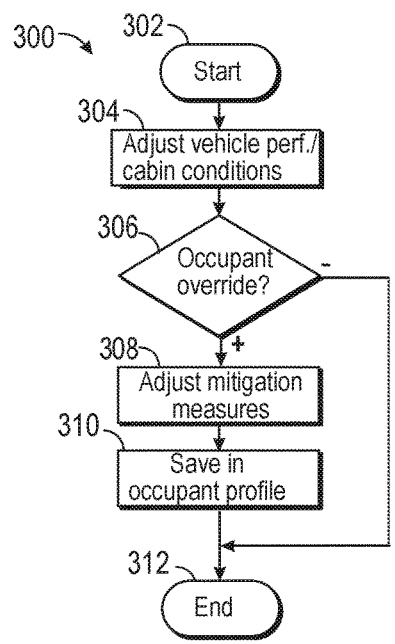
FIG. 5 is a flowchart illustrating a process employing interface modalities and methods for controlling the vehicle of FIG. 1, in accordance with various embodiments.

Referring to FIG. 5, motion sickness mitigation at step 218 of the process 200 may include a number of steps as represented by the process 300. The process 300 may be initiated at step 302 when the process 200 proceeds to steps 216 and 218 from step 214, from step 230, or from step 232. In the current embodiment, process 300 may be initiated when the mitigation module 138 receives the mitigate signal 152 or 162. Proceeding to step 304, the process 300 adjusts vehicle performance and/or cabin conditions to mitigate motion sickness. For example, the mitigation module 138 provides vehicle performance signal 174 to control the actuator system 30 to modify the response of the accelerator actuator 70, the shift actuator 72, the steering actuator 74, the brake actuator 76, the suspension actuator 79 and/or the other actuators 78 to modify the performance of the associated vehicle systems. In a number of examples this is accomplished by selecting a less aggressive driving profile 140 from available options stored in the storage device 118. The level of modification may be selected commensurate with the calculated MSV value and its indication of predicted motion sickness. In addition, the mitigation module 138 provides a cabin condition signal 176 to adjust cabin conditions to mitigate motion sickness. For example, the cabin condition signal 176 may alter operation of the HVAC system 100 to change cabin temperature and airflow. In a number of examples, the cabin temperature may be reduced and/or the airflow may be increased. In a number of examples, when cabin temperature is higher than 72 degrees Fahrenheit (F), it is decreased to 72 degree. When the cabin temperature is not higher than 72 degrees, it is decreased by 3 degrees F. Also at step 304, cabin lighting may be adjusted as a result of the cabin condition signal 176 to alter operation of the lighting system 102. This may be based on a selected light color/quality stored in the occupant profile 148, or a lighting effect stored in storage device 118 with the occupant profile 148. In a number of examples, the light color may be modified such as by increasing the blue content, which is found to have a calming effect. Also at step 304, in a number of examples, aroma therapy is used in the cabin of the vehicle 20. The cabin condition signal 176 may be provided to the HVAC system 100 to trigger the release of an aroma to mitigate motion sickness. The aroma and its intensity may be selected from a preference from the occupant profile 148, or may be selected by the processor 114 based on the MSV value.

In a number of examples, the motion sickness mitigation system 22 operates the suspension system 27 in an active mode through the suspension actuator 79, to mitigate motion sickness. Oscillation of the body 42 on the suspension 27 relative to the wheels 25 has an impact on the onset of motion sickness. Oscillation of the body 42 in the range of 0.08 to 0.22 hertz has been found to be undesirable, with a peak influence found at 0.20 hertz. Accordingly, the mitigation module 138 processes the vehicle state input signal 158 including inputs from the suspension system 27 and delivers the vehicle performance signal 174 to adjust the suspension system 27 with a greater or lesser stiffness to transition oscillations of the body away from the 0.08 to 0.22 hertz range, into a higher or lower oscillation frequency. The suspension actuator 79 may control the level of damping imparted by the suspension system 27 for example, through selected graduated modes or through active control.

Proceeding to step 306, a determination is made as to whether the occupant chooses to adjust or override certain aspects of the mitigation regimen implemented at step 304. For example, the mitigation module provides an adjustment inquiry signal 178 to the interface 98 and the occupant may input changes through the interface 98 to modify the vehicle performance and or cabin condition mitigation measures. When the occupant chooses to make no inputs at step 306, a negative determination results and the process 300 proceeds to step 312 and ends. When the process 300 is part of the process 200, this results in a return to steps 220, 222, 224 and ongoing monitoring and evaluation is conducted. When the occupant chooses to make inputs at step 306, the process 300 proceeds to step 308, where the vehicle performance and/or cabin condition mitigation measures are adjusted according to the occupant's selections. The mitigation module 138 provides the adjustment inquiry signal 178, and receives the occupant inputs through the data input signal 146. In response to the occupant's selection communicated through the data input signal 146, the mitigation module 138 effects implementation of the selection through the vehicle performance signal 174, such as to the actuator system 30, the HVAC system 100, the lighting system 102, and/or the other vehicle systems. The process 300 proceeds to step 310 where the occupant selections made at step 306 are represented and saved in the occupant profile 148. For example, the save signal 180 is provided from the mitigation module 138 to the storage device 118 and the selections are stored as part of the occupant profile 148, and the process 300 ends at step 312. When the process 300 is part of the process 200, it proceeds to steps 220, 222, 224 and ongoing monitoring and evaluation is conducted.

Figure 6:
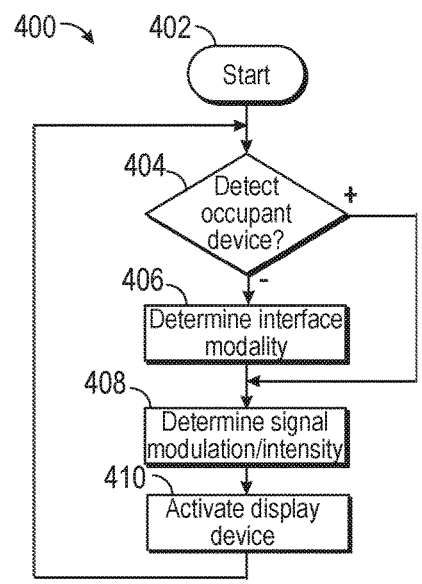
FIG. 6 is a flowchart illustrating a process employing motion sickness mitigation methods for controlling the vehicle of FIG. 1, in accordance with various embodiments.

In a number of embodiments as illustrated in FIG. 6, a process 400 determines the interface modality for communicating with an occupant of the vehicle 20, and alerts the occupant using the selected modality, of incipient vehicle performance aspects. The process 400 may be a part of the process 200, or the process 400 may operate separately. The purpose of the alert is to minimize sensory mismatch of sensed vehicle movements, to reduce or avoid the onset of motion sickness by notifying the occupant before a vehicle performance event occurs. The interface modality module 136 of the control system 130 is supplied with the occupant state input signal 160. In addition, the driving induced motion sickness prediction module 134 may provide an initiate signal 172 to the interface modality module 136, such as when the occupant reports motion sickness at step 230, or when motion sickness is predicted at step 232. The process 400 may be initiated at step 402 in response to either the occupant state input signal 160 or the initiate signal 172. In other embodiments, the process 400 is initiated at step 402 when an occupant profile 148 indicates an occupant has a heightened susceptibility to motion sickness. The process 400 proceeds to step 404 where a determination is made as to whether the occupant has a remote/wearable device 109 such as a PED or a wristband through which they may receive alerts. For example, the interface modality module 136 provides a check signal 182, and in response, attempts to establish a link with the remote/wearable device 109 through the transceiver 96. When the determination is positive and the link is established, the remote wearable device 109 is selected to communicate alerts to the occupant and the process 400 proceeds to step 408 where a signal modulation and intensity is determined as further described below.

In a number of embodiments, when the determination at step 404 is negative, and no remote/wearable device is found, the process 400 proceeds to step 406 and a determination of the type of interface modality for alerting the occupant is undertaken. Various types of display devices may be included in the vehicle 20 to alert an occupant to upcoming performance and movements. A display device is any output device of the motion sickness mitigation system 22 that presents information to an occupant in visual, audible, tactile/haptic, or other form.

Figure 7:
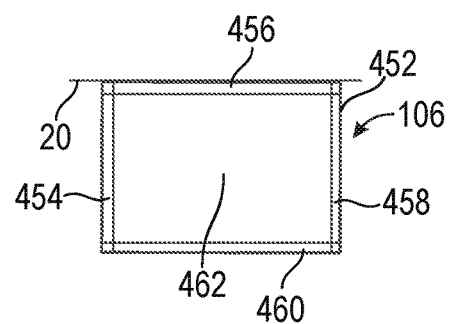
FIG. 7 is an illustration of a visual display system for the motion sickness mitigation system, in accordance with various embodiments.

In a number of examples, as illustrated in FIG. 7, a visual display system 106, such as one with a liquid crystal display or other type of video screen/projection, may be included as the display device in the vehicle 20 for perception by an occupant. The visual display system 106 is located to be readily viewed by a seated occupant. For example, for front seat occupants, the visual display system 106 may be located in the dash, or a head up display may be used. Also for example, for rear seat occupants, the visual display system 106 may be located in the back of a front seat or suspended from the roof of the vehicle 20. The visual display system 106 is configured to display information for an occupant without interfering with other functions of the display device. For example, the perimeter 452 of the visual display system 106 may display information via sectors 454, 456, 458 and 460, while the center 462 remains usable for other purposes. In the current embodiment, the sectors 454, 456, 458 and 460 are in the shape of bars along the perimeter 452, but in other embodiments may take any number of forms. The sectors 454, 456, 458 and 460 are normally not illuminated. In other embodiments, the sectors 454, 456, 458 and 460 may be illuminated to indicate no alerts are present, such as by displaying a green color. To alert an occupant, the sectors 454, 456, 458 and 460 may be illuminated to different light intensities and/or different colors, depending for example, on the level of acceleration force expected from an upcoming vehicle performance action. In some embodiments, a familiar green-yellow red color scheme may be used to alert an occupant to different levels and types of vehicle maneuvers. In some embodiments, a visual message may be provided to the occupant. For example, the occupant is notified to look ahead, such as when a significant deceleration is expected.

Figure 8:
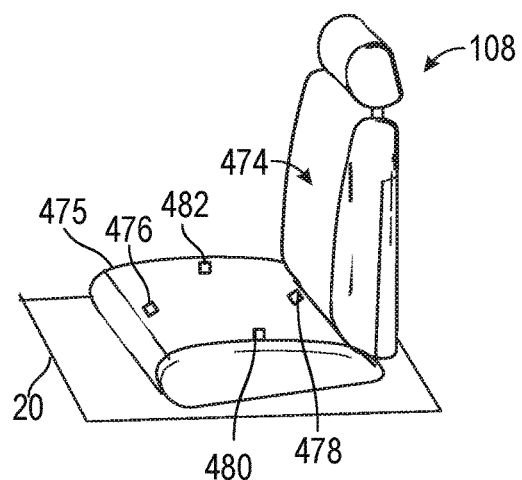
FIG. 8 is an illustration of a haptic display system for the motion sickness mitigation system, in accordance with various embodiments.

In a number of other examples, as illustrated in FIG. 8, a haptic display system 108, such as one with force or vibration generating devices or other type of devices that generate an output perceivable by the sense of touch, may be included as the display devices in the vehicle 20. The haptic display system 108 is located for perception by the occupant, such as in a seat 474. The haptic display system 108 includes components located to be readily felt by a seated occupant and to be perceived as originating in different locations. One haptic device 476 is located at the front of the seat bottom 475. Another haptic device 478 is located at the rear of the seat bottom 475. Two other haptic devices 480, 482 are located on opposite sides of the seat bottom 475. The haptic devices 476, 478, 480, 482 are normally still. To alert an occupant, the haptic devices 476, 478, 480, 482 may be activated individually or in combination and/or to various intensity levels to alert an occupant to different levels and types of vehicle maneuvers.

Figure 9:
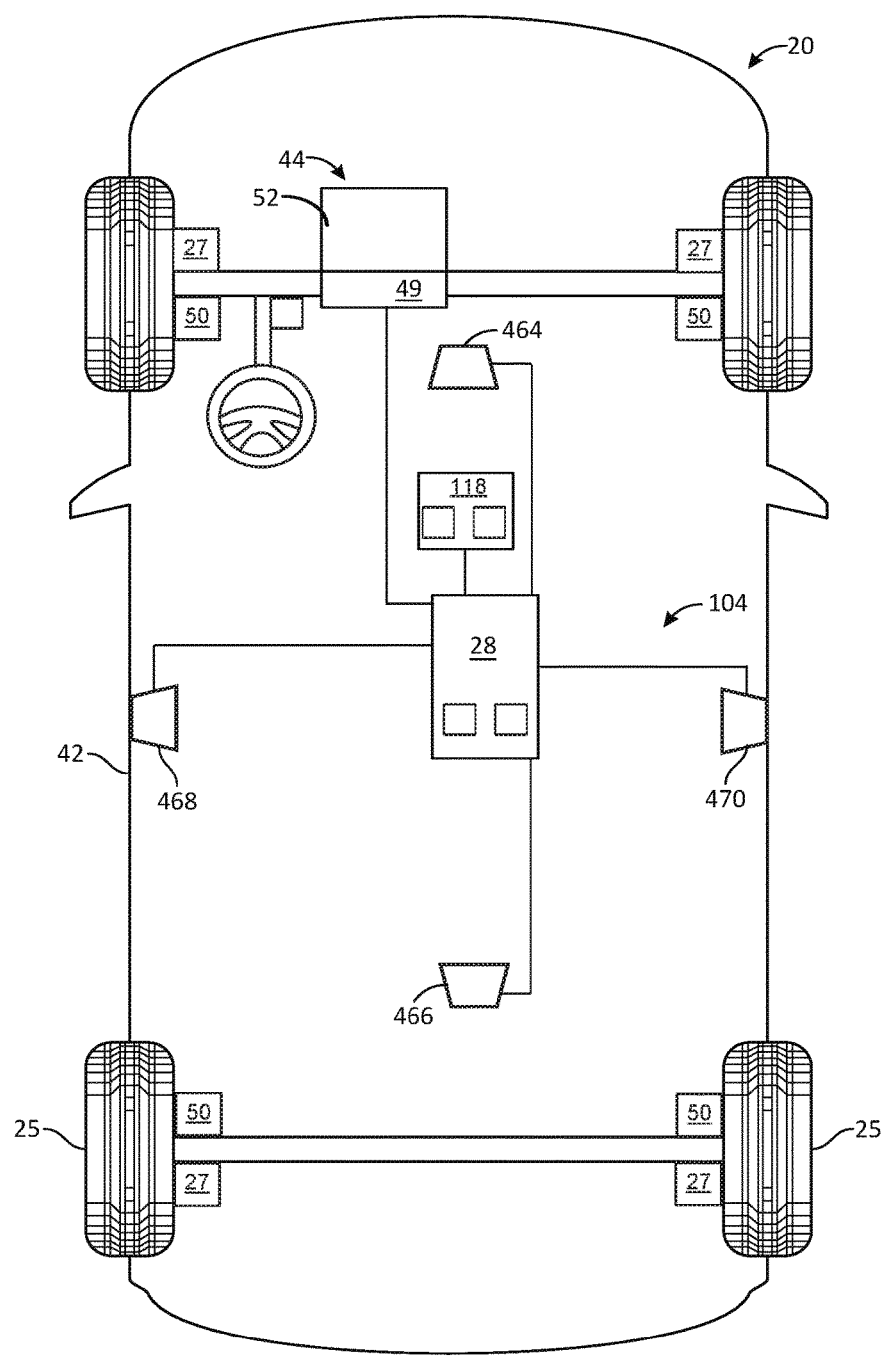
FIG. 9 is an illustration of an audible display system for the motion sickness mitigation system, in accordance with various embodiments.

In a number of other examples, as illustrated in FIG. 9, an audible display system 104, such as one with speakers or other type of sound generator, may be included as the display device in the vehicle 20 for perception by occupants. The audible display system 104 includes components located to be readily heard by a seated occupant and to be perceived as originating in different directions. For example, speakers of the vehicle's sound system may be used, or devices such as piezo or electromagnetic transducers or buzzers, or other devices may be used. One sound generator 464 is located at the front of the passenger compartment of the vehicle 20. Another sound generator 466 is located at the rear of the passenger compartment of the vehicle 20. Two other sound generators 468, 470 are located on opposite sides of the passenger compartment of the vehicle 20. The sound generators 464, 466, 468, 470 are normally silent, or may be in use to provide sounds for other vehicle systems such as an infotainment system. To alert an occupant, the sound generators 464, 466, 468, 470 may be activated to different sound intensity levels and/or different unique sounds. For example, a ping, buzz, or beep sound scheme may be used which is distinguishable from other typical sounds, to alert an occupant to different levels and types of vehicle maneuvers. In some embodiments, a voice message may be provided to the occupant. For example, the occupant is notified to look ahead, such as when a significant deceleration is expected.

Returning to the process 400, at step 406 a determination is made as to whether to use the visual display system 106, the audible display system 104, and/or the haptic display system 108. In response to the initiate signal 172 from the driving induced motion sickness prediction module 134, the interface modality module 136 reads the occupant state input signal 160 and evaluates the state of the occupant. Using input, such as from the motion sensors 92 and the camera 94, the interface modality module discerns the direction the occupant is looking, the position of the occupant, whether the occupant is wearing earphones or headphones, and other aspects of the occupant and their occupation. This may be accomplished through use of the vision system 97. The interface modality is selected based on the occupant's position and the occupation. For example, if the occupant is reclined and their gaze is not directed at the visual display system 106, then the audible display system 104, or the haptic display system 108 is selected. Also for example, if the occupant is wearing headphones and is not looking at the visual display system 106, then the haptic display system 108 is selected. Also for example, if the occupant is looking at the visual display system 106, then it is selected. The process 400 continues to step 410 and the selected display device is activated through a mode selection signal 181 from the interface modality module 136, which may be provided to the activated display system 104, 106, 108, and mode signal 183 is provided to the mitigation module 138. The process continues to monitor in a loop to responds to changes in the occupant's position or occupation.

In a number of examples, the process 200 may use the process 400 to alert an occupant to an upcoming maneuver of the vehicle 20. For example, at step 218, the process 200 presents information about future vehicle movement using the multimodal interface in order to limit visual-vestibular conflict and a mismatch between the occupant's anticipated and the actual vehicle movement. The alert allows an occupant to anticipate and adjust their attention, and be prepared for the future vehicle movement. Future vehicle movement information is available from autonomous control of the vehicle 20. For example, when the controller 28 determines to implement an action to control vehicle performance through the actuator system 30, the expected results of that action are used to alert the occupant. In the case of human driven vehicles, estimates are used to determine when to alert an occupant. For example, if a neighboring vehicle is perceived to take an action by the sensing devices 54, and a driver response is indicated for the vehicle 20, the occupant is alerted to the effect of the driver response, before the driver responds. Once the display device is activated and the interface modality module 136 signals the driving induced motion sickness prediction module 134 of activation, the selected display device remains ready to alert an occupant. The mitigation module 138 processes the input signals 156, 158, 160, 162, 183 and delivers a display signal 185 to alert the occupant via the selected display device. For example, when the vehicle state input signal 158 indicates the vehicle 20 is about to brake and the visual display system 106 is activated, the sector 456 at the screen top of the visual display system 106 is illuminated. The sector 456 is illuminated with greater intensity when the braking level, and thus deceleration of the vehicle 20, is expected to be at a higher level. In a number examples, the sector 456 is illuminated in green when the expected braking level is low, in yellow when the expected braking level is moderate, and in red when the expected braking level is high. In other examples, green may be displayed when no braking is expected. Similarly, when the selected display device is the audible display system 104, the sound generator 464 at the front of the passenger compartment is signaled to generate sound. The sound level is proportional to the level of braking expected. Also similarly, when the selected display device is the haptic display system 108, the haptic device 476 at the front of the seat bottom 475 is signaled to generate perceivable movement. The intensity level is proportional to the level of braking expected. The sector 460, the sound generator 466 or the haptic device 478 is signaled to alert the occupant to forward acceleration of the vehicle 20. The sector 454, the sound generator 468 or the haptic device 480 is signaled to alert the occupant to acceleration of the vehicle 20, to the left. The sector 458, the sound generator 470 or the haptic device 482 is signaled to alert the occupant to acceleration of the vehicle 20, to the right. By alerting the occupant to upcoming vehicle movements, the onset of motion sickness is reduced or avoided. In some embodiments, alerts are provided whenever an occupant in the vehicle 20 has a high level of sensitivity to motion sickness, as indicated by their occupant profile 148. In other embodiments, the alerts are initiated when the MSV passes a threshold that is lower than a point at which initiation of vehicle performance or cabin condition mitigation measures are implemented. In a number of embodiments, the process 400 is initiated when the occupant state devices 88 detect a sensory mismatch between visual and body perceived movement of the vehicle 20, as indicated by body/head/eye movement of the occupant.

Accordingly, when motion sickness is predicted or likely, the motion sickness mitigation system 22 alters vehicle performance, cabin conditions, and/or alerts the occupant to upcoming vehicle actions, to avoid or alleviate motion sickness. While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. A motion sickness mitigation system of a vehicle comprising:
   a steering system of the vehicle including a steering actuator steering the vehicle through the steering system;
   a braking system including a brake actuator actuating the braking system;
   an accelerator system including an accelerator actuator actuating the accelerator system; and
   a controller including a processor configured to:
   receive an occupant profile that includes a biometric condition of an occupant, preferences of the occupant and historical travel information of the occupant in the vehicle,
   receive traffic information for an upcoming trip of the vehicle on a route,
   calculate, using the occupant profile and the traffic information, whether the occupant is likely to experience motion sickness when the vehicle travels on the route, and
   deliver a vehicle performance signal correlated to the calculation, to initiate motion sickness mitigation,
   wherein the vehicle performance signal varies operation of the steering actuator, the accelerator actuator or the brake actuator to implement the motion sickness mitigation.

2. The motion sickness mitigation system of claim 1 comprising a suspension system of the vehicle that includes a suspension actuator through which the suspension system is varied, wherein the vehicle performance signal varies operation of the suspension actuator to implement the motion sickness mitigation.

3. The motion sickness mitigation system of claim 1 comprising a transceiver through which information is received by the controller, wherein the processor is configured to enter the information into the occupant profile.

4. The motion sickness mitigation system of claim 1 wherein the processor is configured to carry out the calculation prior to the vehicle starting on the route.

5. The motion sickness mitigation system of claim 1 comprising:
  occupant state devices configured to provide an occupant state input signal to the processor representing at least one state of the occupant;
  wherein the processor is configured to calculate an occupant motion sickness value based on the occupant state input signal;
  wherein the occupant motion sickness value is indicative of a likelihood that the occupant will experience motion sickness.

6. The motion sickness mitigation system of claim 5 comprising:
  an accelerometer on the vehicle, configured to monitor acceleration of the vehicle and to provide, to the processor, a first vehicle state signal based on the acceleration, when the vehicle operates on the route;
  a steering angle sensor on the vehicle, configured to monitor steering changes of the vehicle and to provide, to the processor, a second vehicle state signal based on the steering changes, when the vehicle operates on the route; and
  a suspension sensor on the vehicle, configured to monitor suspension oscillations of the vehicle and to provide, to the processor, a third vehicle state signal based on the suspension oscillations, when the vehicle operates on the route;
  wherein the processor is configured to calculate a vehicle motion sickness value based on the first, second and third vehicle state signals;
  wherein the vehicle motion sickness value is indicative of the likelihood that the occupant will experience motion sickness.

7. The motion sickness mitigation system of claim 6 wherein the processor comprises a pre-trip prediction module and a driving induced motion sickness prediction module, wherein:
  the pre-trip prediction module is configured to receive the occupant profile and the traffic information and to calculate whether the occupant is likely to experience motion sickness when the vehicle travels on the route; and
  the driving induced motion sickness prediction module is configured to receive the first, second and third vehicle state signals and to calculate the vehicle motion sickness value based on the first, second and third vehicle state signals.

8. A method of motion sickness mitigation in a vehicle comprising:
  receiving, by a processor of a controller, a data input signal that represents an occupant profile that includes a biometric condition of an occupant, preferences of the occupant, and historical travel information of the occupant in the vehicle;
  receiving, by the processor, an off-board input signal representing traffic status for an upcoming trip of the vehicle on a route;
  calculating, by the processor, whether the occupant is likely to experience motion sickness when the vehicle travels on the route, using the data input signal and the off-board input signal; and
  delivering a vehicle performance signal to initiate motion sickness mitigation, wherein the vehicle performance signal varies operation of a steering actuator of the vehicle, an accelerator actuator of the vehicle, or a brake actuator of the vehicle when the vehicle operates on the route, to implement the motion sickness mitigation.

9. The method of claim 8 comprising:
  monitoring a suspension system of the vehicle that includes a suspension actuator through which the suspension system is varied; and
  altering operation of the suspension actuator, via the vehicle performance signal, to implement the motion sickness mitigation.

10. The method of claim 8 comprising:
  receiving, by the processor, information from the occupant via a transceiver; and
  delivering, by the processor, the information to a storage device for storage in the occupant profile.

11. The method of claim 8 comprising calculating whether the occupant is likely to experience motion sickness when the vehicle travels on the route, prior to the vehicle starting on the route.

12. The method of claim 8 comprising:
  delivering an occupant state input signal, by occupant state devices, to the processor, wherein the occupant state input signal represents at least one state of the occupant; and
  calculating, by the processor, an occupant motion sickness value ($MSV_o$) based on the occupant state input signal, wherein the occupant motion sickness value is indicative of a likelihood that the occupant will experience motion sickness.

13. The method of claim 12 wherein calculating the $MSV_o$ comprises:
  obtaining, by the processor from the occupant profile, a susceptibility value indicative of the occupant's susceptibility to motion sickness;
  receiving, by the processor from the occupant state devices, a heart rate of the occupant, a respiration rate of the occupant; skin resistance of the occupant, skin temperature of the occupant, blood pressure of the occupant, and a facial expression of the occupant; and
  calculating, by the processor, the $MSV_o$ using the heart rate, the respiration rate, the skin resistance, the skin temperature, the blood pressure and the facial expression, wherein the $MSV_o$ is indicative of the likelihood that the occupant will experience motion sickness.

14. The method of claim 12 comprising:
  monitoring, by an accelerometer, acceleration of the vehicle when the vehicle operates on the route;
  delivering, from the accelerometer to the processor, a first vehicle state signal based on the acceleration;
  monitoring, by a steering angle sensor on the vehicle, steering changes of the vehicle when the vehicle operates on the route;
  delivering, from the steering angle sensor to the processor, a second vehicle state signal based on the steering changes;
  monitoring, by a suspension sensor, suspension oscillations of the vehicle when the vehicle operates on the route;

delivering, from the suspension sensor to the processor, a third vehicle state signal based on the suspension oscillations; and calculating, by the processor a vehicle motion sickness value ($MSV_v$) based on the first, second and third vehicle state signals.

15. The method of claim 14 comprising:

monitoring, by sensing devices in the vehicle, cabin conditions of the vehicle; and calculating, by the processor, a cabin condition state value (C) based on the cabin conditions, wherein the C is indicative of the likelihood that the occupant will experience motion sickness.

16. The method of claim 15 comprising:

calculating, by the processor, an aggregate motion sickness value (MSV) by the equation $MSV=MSV_v \times MSV_o \times C$, wherein the MSV is indicative of the likelihood that the occupant will experience motion sickness.

17. The method of claim 16 wherein the motion sickness mitigation is implemented when the MSV exceeds a threshold value.

18. The method of claim 8, wherein the motion sickness mitigation comprises activating, by the processor, a display to alert the occupant to an upcoming vehicle maneuver to avoid a mismatch between sensed movements of the vehicle by the occupant.

19. The method of claim 18 wherein the display comprises a visual display system, an audible display system and a haptic display system and comprising:

delivering an occupant state input signal, by occupant state devices, to the processor, wherein the occupant state input signal represents states of the occupant;

evaluating, by the processor, the states of the occupant to discern a gaze, a position, and a presence of the occupant; and selecting, by the processor, among the visual display system, the audible display system and the haptic display system based on the gaze, the position and the occupation.

20. A motion sickness mitigation system of a vehicle comprising:

an acceleration sensor sensing acceleration of the vehicle and generating an acceleration signal representative of the sensed acceleration;

a camera configured to observe an occupant of the vehicle and providing a visual signal representative of the occupant;

a controller receiving the acceleration signal and the visual signal and including a processor, the processor configured to:

discern, from the visual signal a direction the occupant is looking;

select an interface modality based on the direction; and communicate with the occupant through the interface modality; and an actuator device responsive to the processor, wherein the actuator device controls performance of a vehicle system;

wherein the processor is configured to calculate whether the occupant is likely to experience motion sickness based on the acceleration signal and the visual signal;

wherein the processor controls the actuator device in a variable manner depending on whether the calculation indicates the occupant is likely to experience motion sickness.

* * * * *